US008580979B1

(12) United States Patent
Shulgin

(10) Patent No.: US 8,580,979 B1
(45) Date of Patent: Nov. 12, 2013

(54) METHOD OF PREPARING A HUMIC ACID EXTRACTION

(71) Applicant: Organocat, LLC, Louisville, KY (US)

(72) Inventor: Alexander Shulgin, Louisville, KY (US)

(73) Assignee: Organocat, LLC, Louisville, KY (US)

( * ) Notice: Subject to any disclaimer, the term of this patent is extended or adjusted under 35 U.S.C. 154(b) by 0 days.

(21) Appl. No.: 13/746,027

(22) Filed: Jan. 21, 2013

Related U.S. Application Data

(62) Division of application No. 12/884,349, filed on Sep. 17, 2010, now abandoned.

(60) Provisional application No. 61/246,331, filed on Sep. 28, 2009.

(51) Int. Cl.
 *C07D 319/00* (2006.01)
 *B01D 53/14* (2006.01)
(52) U.S. Cl.
 USPC .................. 549/359; 423/210; 423/215.5
(58) Field of Classification Search
 USPC ............................................. 44/490; 549/359
 See application file for complete search history.

(56) References Cited

U.S. PATENT DOCUMENTS

| | | | |
|---|---|---|---|
| 3,900,554 A | 8/1975 | Lyon | |
| 4,237,101 A * | 12/1980 | Willard, Sr. | ............. 44/490 |
| 4,261,809 A | 4/1981 | Gorin et al. | |
| 4,288,420 A | 9/1981 | Ito et al. | |
| 4,459,149 A * | 7/1984 | Moran et al. | ............. 71/24 |
| 4,911,900 A | 3/1990 | Horch et al. | |
| 5,009,697 A * | 4/1991 | Martin et al. | ............. 71/24 |
| 5,058,514 A | 10/1991 | Mozes et al. | |
| 5,352,370 A | 10/1994 | Hayden | |
| 5,441,713 A | 8/1995 | Dubin et al. | |
| 5,443,613 A | 8/1995 | Robinson | |
| 5,494,869 A | 2/1996 | Hayden et al. | |
| 5,674,462 A | 10/1997 | Hayden et al. | |
| 5,700,436 A | 12/1997 | Doughty et al. | |
| 5,733,515 A | 3/1998 | Doughty et al. | |
| 6,083,293 A | 7/2000 | Bath | |
| 6,114,273 A | 9/2000 | Hayden | |
| 6,696,577 B1 * | 2/2004 | Westwood | ............. 549/359 |
| 6,722,295 B2 | 4/2004 | Zauderer | |
| 6,773,555 B1 | 8/2004 | Izutsu et al. | |
| 7,204,660 B2 | 4/2007 | Shulgin | |
| 7,524,472 B1 | 4/2009 | Kong | |
| 7,825,266 B1 * | 11/2010 | McMahon | ............. 549/359 |
| 2004/0020107 A1 * | 2/2004 | Chapman | ............. 44/490 |
| 2004/0213720 A1 | 10/2004 | Wolf et al. | |
| 2010/0189618 A1 | 7/2010 | White et al. | |

FOREIGN PATENT DOCUMENTS

| | | |
|---|---|---|
| DE | 3526756 | 1/1987 |
| DE | 3800730 | 8/1988 |
| EP | 264041 | 4/1988 |

* cited by examiner

*Primary Examiner* — Wayne Langel
(74) *Attorney, Agent, or Firm* — Camoriano and Associates; Therese Camoriano

(57) ABSTRACT

Humic Acid is extracted and then can be used to treat flue gas and fly ash from the combustion of coal or municipal waste. The resulting product may be used as a soil ameliorant.

4 Claims, 2 Drawing Sheets

METHOD OF PREPARING A HUMIC ACID EXTRACTION

BACKGROUND

This application is a Divisional of U.S. application Ser. No. 12/884,349, filed Sep. 17, 2010 which claims priority from U.S. Provisional Application Ser. No. 61/246,331, filed Sep. 28, 2009.

The present invention relates to the preparation of a humic acid extraction which may be used for removing acidic gases from a flue gas stream and for soil amelioration.

DESCRIPTION

Figure 1:
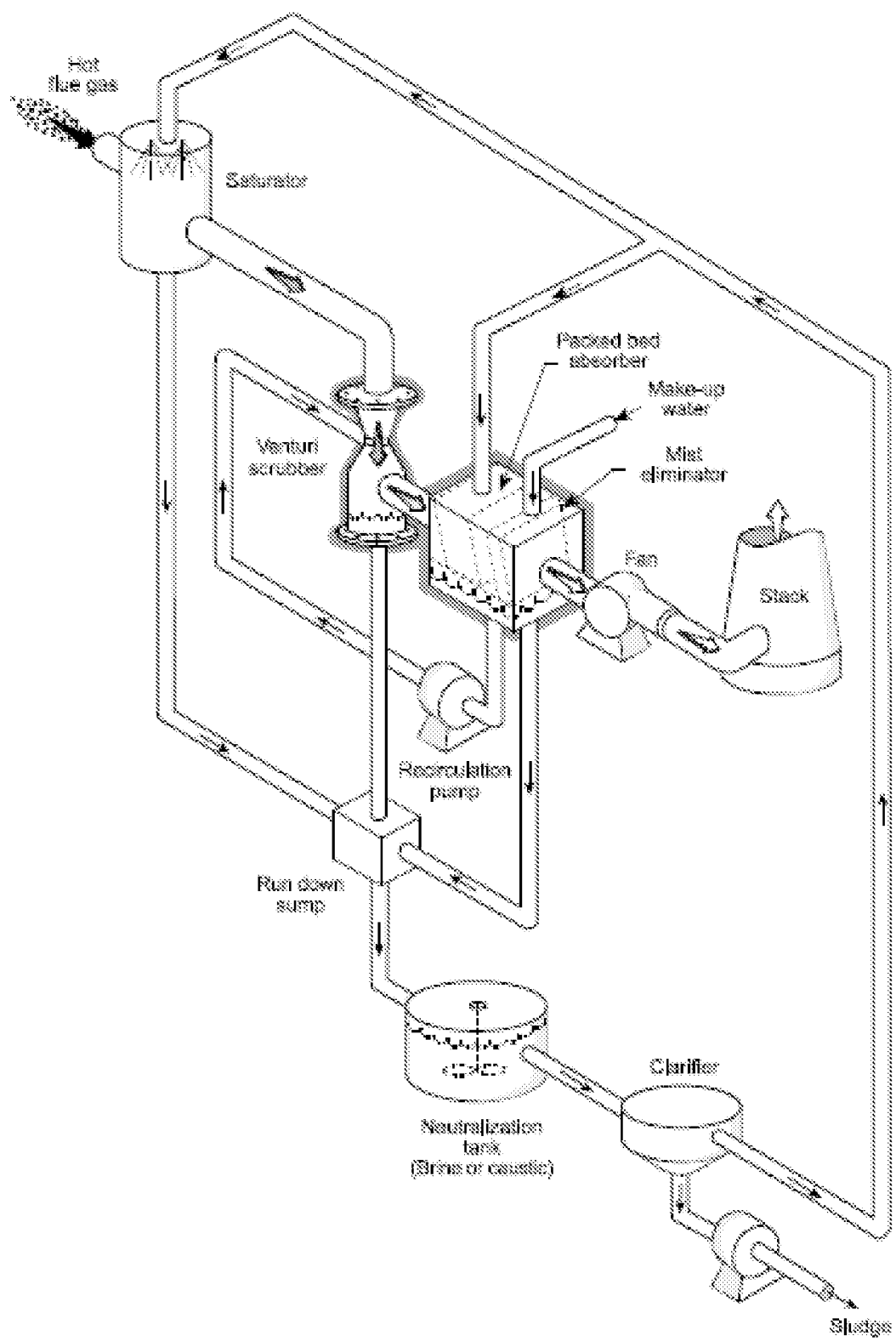
FIG. 1 is a schematic drawing of a wet scrubbing system which may be used to carry out the present invention.

Three basic processes involving the use of Humic Acid are described below. One process involves reacting Humic Acids with Sodium hydroxide or Potassium hydroxide and applying the resulting material to the flue gas stream. Another process involves reacting Humic Acids with anhydrous ammonia or aqueous ammonia and applying the resulting material to the flue gas, and the third process involves reacting Humic Acid with a urea solution and applying that material to the flue gas.

Humic Acid sources include brown coal (leonardite or lignite), peat, composts, and bottom sediments in lakes, rivers, etc. Brown coal is readily available, especially where it is used in energy production. Brown coal contains Humic Acids that are highly oxidized organic matter, and hydrocarbons called bitumen, that is highly reduced organic matter, as well as mineral carbon, aluminum silicates, macro and micro amounts of iron, manganese, and other elements. These can be represented by the following schematic formula: Rm . . . Rh . . . HumH, with Rm representing mineral compounds, Rh representing hydrocarbon compounds and HumH representing Humic Acids. Rh can be represented as CnHm or in other words it is hydrocarbons which include carbon C and hydrogen H.

In the schematic formula HumH, Hum represents polycyclic and aliphatic organic carbon structures and H represents Hydrogen (protons) that are available for chemical interaction. Originally, Humic Acids have no chemical activity in their native state.

Humic Acids can be dissolved in alkali solutions, such as sodium, potassium and ammonium hydroxides as well as sodium, potassium and ammonium bicarbonates or carbonates. Sodium, potassium and ammonium cations in the hydroxide state or bicarbonate/carbonate state are able to replace the protons into Humic Acid molecules resulting in their dissolution and activation. It is an extraction process resulting in the conversion of insoluble Humic Acids to soluble salts, e.g., Sodium Humate, Potassium Humate and Ammonium Humate. Humic Acids are very soluble in anhydrous ammonia and urea solutions. When humic acids are dissolved in anhydrous ammonia, they form Ammonium Humate and dissolved Humic Acid in the anhydrous ammonia. In urea solutions, the Humic Acid is only dissolved, meaning that the Humic Acids are transferred to a soluble state without significantly changing their chemical composition.

Bitumen hydrocarbons have their specific melting and boiling temperature and their basic properties include melting and conversion to gaseous form above the boiling temperature.

The basic property of mineral carbon is to serve as an adsorbent.

The basic property of the Metallic compounds is to serve as a catalyst.

In some examples described below, a material containing Humic Acids, for instance brown coal, is ground to a particle size of about 0.1 millimeters or less prior to mixing it with a liquid. When mixed with the liquid, the Humic Acids are activated through dissolution and extraction. Four examples are described here.

The first is to mix with Sodium or Potassium hydroxide, the second is to mix with Anhydrous Ammonia, the third is to mix with Aqueous Ammonia, and the fourth is to mix with Urea.

1. Treatment of Humic Acids with Sodium or Potassium Hydroxide

Sodium or potassium hydroxides in the dry or liquid forms are the basic material for the treatment of Humic Acids sources. Primary bituminous brown coal is put into a blender with Sodium or Potassium hydroxide solution and is mixed until stable slurry is formed. The preferred ratio of coal to sodium or potassium hydroxide solution is from 1:4 to 1:20 by mass. The preferred temperature range is about 65-95 C. The interaction of Humic Acids with sodium or potassium hydroxide may be described by the next schematic equation:

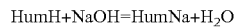

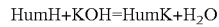

This is an ion exchange mechanism. This process forms alkali sodium humate HumNa or potassium humate HumK, which are sodium and potassium salts of Humic Acids. Note: Sodium or potassium carbonates/bicarbonates also can be used, resulting in formation of the same sodium or potassium Humates. They are very soluble substances. The slurry also contains some excessive amount of sodium hydroxide or potassium hydroxide as well as hydrated and hydrolyzed coal particles in which there is bitumen, mineral carbon, iron, manganese, etc. oxides and hydroxides, and water. The slurry chemical composition can be represented by the schematic formula: Rm . . . Rh . . . HumNa . . . $H_2O$ or Rm . . . Rh . . . HumK . . . $H_2O$. The slurry can readily be pumped into the flue gas stream in order to neutralize nitrous oxides, sulfur oxide and hydrogen sulfate. It also is possible to separate the particulate matter and use the liquid solution that has been separated from the particles as opposed to using the whole slurry with particles. The separation may be accomplished by settling, filtering, centrifuging, or using other known physical separation methods. The liquid solution does not contain bitumen and can be readily and easily pumped into the flue gas stream for the neutralization of sulfur oxides and hydrogen sulfate.

If a wet scrubbing system as shown in FIG. 1 is used, the slurry or separated liquid solution would be put into the neutralization tank and then injected into the saturator, where it would be sprayed to contact the hot flue gas. Additional slurry or separated liquid solution would be added in the make-up water line.

Figure 2:
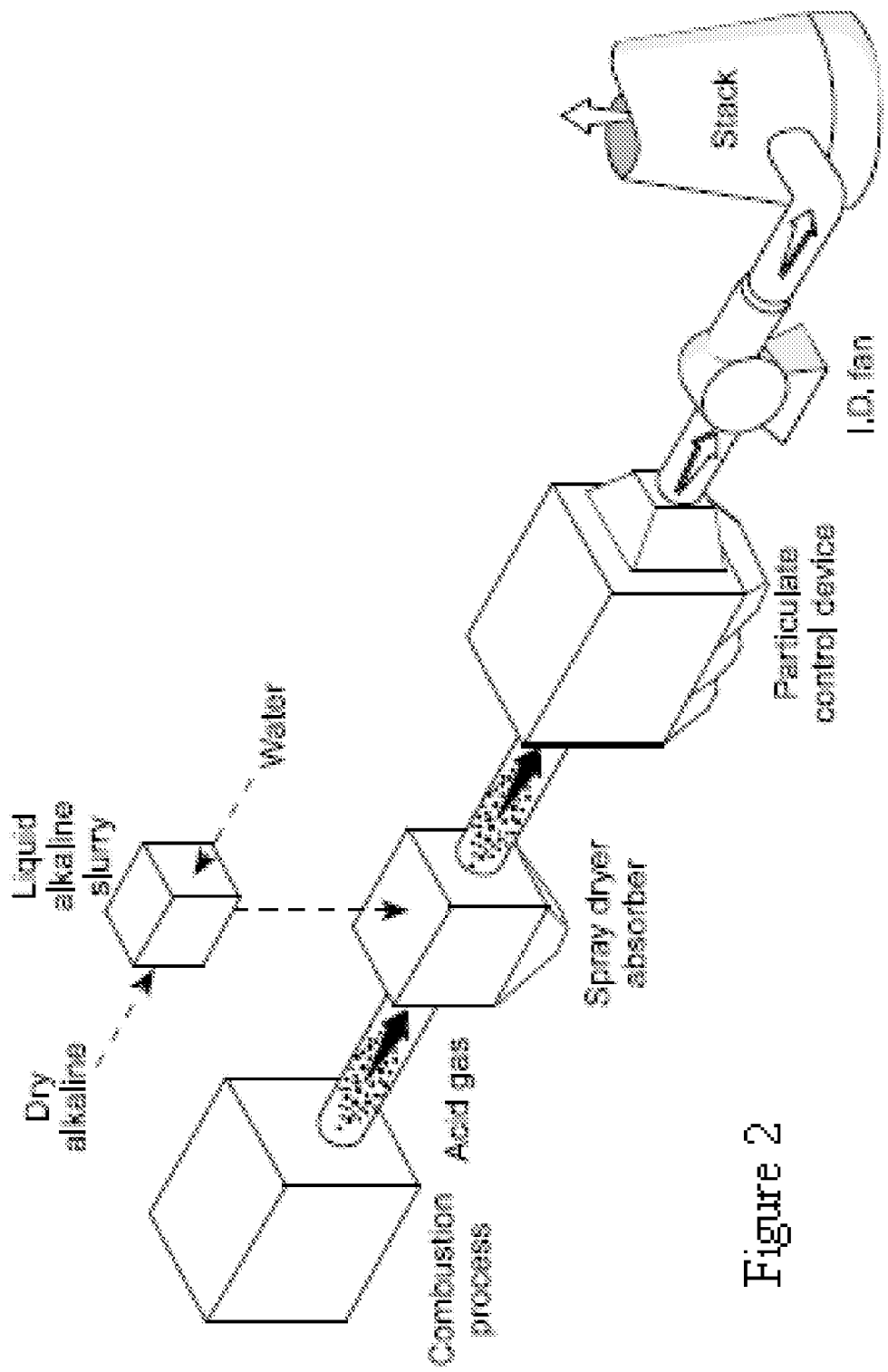
FIG. 2 is a schematic drawing of a spray dryer absorber system which may be used to carry out the present invention.

If a spray dryer absorber system as shown in FIG. 2 is used, the slurry or separated liquid solution would be inserted as the liquid alkaline slurry into the spray dryer absorber.

2. Treatment of Humic Acids with Anhydrous Ammonia

Anhydrous Ammonia is a liquid under pressure and can be blended with ground brown coal under the same or lower pressure. Brown coal is ground to a particle size of about 0.1 millimeters in diameter or less and initially is loaded into the tank with impeller/propeller or other type of mixing system that is designed to work under pressure and then liquid anhydrous ammonia is pumped into the same tank under a pressure above atmospheric pressure, and mixing is started. The mixing process takes from several minutes to several tens of minutes.

There are two mechanisms of Ammonia interaction with Humic Acids. The first is based upon ammonia conversion to ammonium due to coal water content. The water content of regular brown coal is around 30-45% due to the high hydrophilicity of Humic Acids. Dried brown coal water content is around 11-18%. The water in the coal is available for interaction with the ammonia, resulting in the formation of ammonium hydroxide. The solubility of Ammonia in water is 25% (by mass). This means that the mass Q of liquid ammonia that may be mixed with the ground brown coal sufficient to interact with the existing water in the coal is determined according to following equation:

$$Q=0.25WM,$$

where
W—water content in ground brown coal,
M—brown coal mass.

As indicated above, the liquid ammonia mass determined by the equation will be absorbed by the coal without liquid phase formation. The resulting product would not be a liquid and could not be pumped to be applied into the flue gas stream. Therefore, more Anhydrous ammonia is added in order to make the result liquid enough that it can be pumped. The preferred ratio between brown coal and Anhydrous ammonia is from 1:7 to 1:26 (mass). This ratio range allows the formation of a liquid product that can be pumped into the flue gas stream. This material contains Ammonium Humate (see below), dissolved Humic Acids and liquid Ammonia. The term Ammonia Humate is applicable here. This material can be applied into the flue gas stream under pressure to avoid gaseous ammonia formation that is flammable and explosive.

The need to keep the product under pressure to avoid the formation of gaseous ammonia can be avoided by using Aqueous Ammonia instead of Anhydrous Ammonia, as described below.

3. Treatment of Humic Acids with Aqueous Ammonia

Anhydrous ammonia is an original product for the production of aqueous ammonia (ammonia water, ammonium hydroxide) through its dissolution into water. It is a reversible process according to the following equation:

$$NH_3+H_2O=NH_4OH=NH_4^+ +OH^-=NH_3+H_2O$$

It can be dissolved 25% (mass) ammonia in water which converts to ammonium. The pH of Ammonium hydroxide is about 11.8, and ammonia releases from this solution even under normal conditions. The lower the pH, the less ammonia releases from the solution. If the pH is below 7, there is insignificant ammonia release from the solution. The rate of ammonia release also depends on temperature. Higher temperatures increase ammonia release from the solution. Room temperature is preferred for this process.

Once prepared, ammonium hydroxide is available to be blended with ground brown coal, and the coal water content does not make a big difference. Brown coal is put into the blender with ammonium hydroxide and is blended until a stable slurry is formed. A preferred ratio of coal to ammonium hydroxide by mass is from 1:6 to 1:20. Again, this process is carried out at room temperature. The Humic Acids in the brown coal interact with the ammonium according to the next equation:

$$HumH+NH_4OH=HumNH_4+H_2O$$

This is an ion exchange mechanism. This process forms ammonium humate $HumNH_4$, which is a very soluble substance. It is an ammoniacal salt of the Humic Acids. It is an alkaline solution in which ammonia is bound more strongly, but is still available for release from the solution. The slurry also contains excess amounts of dissolved ammonia, hydrated and hydrolyzed coal particles in which there is some bitumen, mineral carbon, iron, manganese, etc. oxides and hydroxides, and water. The slurry chemical composition can be represented by the schematic formula: $Rm \ldots Rh \ldots HumNH_4 \ldots H_2O$. This slurry can readily be pumped into the flue gas stream. It also is possible to separate the particulate matter and use the liquid solution that has been separated from the particles as opposed to using the whole slurry with particles. The separation may be accomplished by settling, filtering, centrifuging, or using other known physical separation methods.

4. Treatment of Humic Acids with Urea Solution

Liquid urea is a good solvent for Humic Acids. Solid urea is dissolved in water to form the liquid urea. Brown coal is ground to a particle size of about 0.1 millimeters in diameter or less, is put into the blender with the liquid urea and is mixed until a stable slurry is formed. It is preferred that the urea be about half of the solution (mass). The preferred ratio of coal to liquid urea is from 1:6 to 1:20 by mass. The preferred temperature range is about 65-95 C. The dissolution of Humic Acids in the liquid urea may be described by the next schematic equation:

$$HumH+[H_2O \ldots (NH_2)_2CO \ldots H_2O]=[H_2O \ldots HumH \ldots (NH_2)_2CO \ldots HumH \ldots H_2O]$$

This is not an ion exchange mechanism. It is just Humic acid dissolution due to strong hydrogen bonds between water, urea and Humic Acid molecules. The term "Urea Humate" is applicable for this solution. It is a neutral solution in terms of its pH or it may be an alkali solution due to urea volatilization and its partial conversion into ammonium/ammonia. This solution would release urea in gas form and ammonia at high temperature. The slurry also contains hydrated coal particles in which there is some bitumen, mineral carbon, iron, manganese, etc. It may be represented by the schematic formula: $Rm \ldots Rh \ldots HumH \ldots (NH_2)_2CO \ldots H_2O$. The resulting slurry may be pumped into the flue gas stream. It is also possible to separate the particulate matter by one or more physical methods, as described above, and use the solution that has been separated from the particles as opposed to using the whole slurry with particles.

Application to the Flue Gas Stream:

The present invention does not require changing anything in the existing system of flue gas treatment in coal and other fossil fuel burning facilities, municipal waste incinerators, etc. The Sodium Humate or Potassium Humate, Ammonia Humate or Ammonium Humate or Urea Humate slurry or solution may simply be pumped and sprayed into the flue gas stream of the wet scrubbing system or the spray dryer absorber system as shown in the attached figures.

Instead of using reducing agents such as ammonia/ammonium or urea for the conversion of nitrogen oxides to environmentally neutral nitrogen, this arrangement uses Sodium Humate or Potassium Humate (slurry only), Ammonia Humate or Ammonium Humate (slurry or solution) or Urea Humate (slurry or solution). Instead of using lime (calcium carbonate or calcium oxide/hydroxide) or other alkali materials for the neutralization of sulfur dioxide and hydrogen chloride, it uses the same Sodium Humate or Potassium Humate, Ammonia Humate or Ammonium Humate or Urea Humate for sulfur dioxide and hydrogen chloride neutralization. So, only one material needs be used, as compared with other processes which require, as a minimum, two different reagents.

In the case of Sodium Humate and Potassium Humate, the following reactions occur:

For Sodium Humate:

$$Rm\ldots Rh\ldots HumNa\text{ --- (temperature) --- }Rm\ldots HumNa+CnHm\text{ (gas)}$$

$$NO_x+CnHm\text{ --- }N_2+CO_2+H_2O$$

For Potassium Humate:

$$Rm\ldots Rh\ldots HumK\text{ --- (temperature) --- }Rm\ldots HumK+CnHm\text{ (gas)}$$

$$NO_x+CnHm\text{ --- }N_2+CO_2+H_2O$$

Under high temperature, bitumen hydrocarbons that are originally solid or soft convert to the gaseous form and release from the coal particles which are within the slurry. Hydrocarbons CnHm (gas) reduce nitrogen oxides to nitrogen.

Note: It is possible to form the neutral sodium nitrate NaNO3 under strong aerobic conditions. Ammonium nitrate is a nitrogen fertilizer.

Sodium Humate or Potassium Humate interact with sulfur dioxide and hydrogen chloride according to the next schematic equation:

$$SO_2+H_2O+HumNa+NaOH\text{ --- }HumH+Hum(H)_n(SO_4)_m+Na_2SO_4$$

$$SO_2+H_2O+HumK+KOH\text{ --- }HumH+Hum(H)_n(SO_4)_m+K_2SO_4$$

Acidic $SO_2$ converts Sodium Humate or Potassium Humate to Humic Acids (which coagulate) and forms $Hum(H)_n(SO_4)_m$, which is Humic Acids-sulfates complex substance, and sodium sulfate Na2SO4 or potassium sulfate $K_2SO_4$.

$$HCl+H_2O+HumNa+NaOH\text{ --- }HumH+Hum(H)_nCl_m+NaCl+H_2O$$

$$HCl+H_2O+HumK+KOH\text{ --- }HumH+Hum(H)_nCl_m+KCl+H_2O$$

Acidic HCl converts Sodium Humate or Potassium Humate to Humic Acids (which coagulate) and forms $Hum(H)_nCl_m$ which is Humic Acids—chlorides complex substance, and sodium chloride NaCl or potassium chloride KCl. Potassium sulfate and potassium chloride are valuable fertilizers. There is also a mechanism of carbon dioxide absorption according to the following equation:

$$CO_2+[HumNa+NaOH]\text{ --- }HumNa+NaHCO_3+H_2O$$

$$CO_2+[HumNa+NaOH]\text{ --- }HumNa+Na_2CO_3+H_2O$$

Carbon dioxide converts to sodium bicarbonate or sodium carbonate. The same process works for alkali Potassium Humate resulting in carbon dioxide conversion to potassium bicarbonate or carbonate.

After water evaporates from the resulting slurry, the final material including all the compounds described above is a powder that is collected together with fly ash in a bag house. In the case of Ammonia Humate or Ammonium Humate, the following reaction occurs:

$$NO_x+[HumNH_4+NH_4OH]\text{ --- }N_2+HumH+HumNH_4+NH_4OH+H_2O$$

Note: It is possible to form the neutral ammonium nitrate NH4NO3 under strong aerobic conditions. Ammonium nitrate is a valuable nitrogen fertilizer.

Ammonia reduces nitrogen oxides to nitrogen. At the same time, acidic $NO_x$ converts some Ammonium Humate to Humic Acids. The remaining part of Ammonium Humate interacts with acidic sulfur dioxide and hydrogen chloride according to the next schematic equations:

$$SO_2+H_2O+[HumNH_4+NH_4OH]\text{ --- }HumH+Hum(H)_n(SO_4)_m++(NH_4)_2SO_4$$

Acidic $SO_2$ converts Ammonium Humate to Humic Acids (which coagulate) and forms $Hum(H)_n(SO_4)_m$, which is Humic Acids-sulfates complex substance, and ammonium sulfate $(NH_4)_2SO_4$ which is a valuable nitrogen fertilizer.

$$H_2O+HCl+[HumNH_4+NH_4OH]\text{ --- }HumH+Hum(H)_nCl_m+NH_4Cl.$$

Acidic HCl converts Ammonia Humate to Humic Acids (which coagulate) and forms $Hum(H)_nCl_m$ which is Humic Acids—chlorides complex substance, and ammonium chloride, which is a nitrogen fertilizer. There is also a mechanism of carbon dioxide absorption according to the next equation:

$$CO_2+[HumNH_4+NH_4OH]\text{ --- }HumNH_4+NH_4HCO_3+H_2O$$

$$CO_2+[HumNH_4+NH_4OH]\text{ --- }HumNH_4+(NH_4)_2CO_3+H_2O$$

Carbon dioxide converts to ammonium bicarbonate or ammonium carbonate which are valuable nitrogen fertilizers.

After water evaporates from the resulting slurry, the final material including all described above compounds is a powder that is collected together with fly ash in a bag house.

In the case of Urea Humate application, the following reaction occurs:

$$NO_x+[H_2O\ldots HumH\ldots(NH_2)_2CO\ldots HumH\ldots H_2O]\text{ --- }N_2+CO_2++HumH+[HumH\ldots(NH_2)CO\ldots HumH]+H_2O$$

Urea reduces nitrogen oxides to nitrogen. At the same time, acidic $NO_x$ converts some dissolved Humic Acids to solids. The remaining part of Ammonium Humate interacts with sulfur dioxide and hydrogen chloride according to the following schematic equations:

$$H_2O+SO_2+[H_2O\ldots HumH\ldots(NH_2)_2CO\ldots HumH\ldots H_2O]\text{ ------ }HumH\ldots(NH_2)_2CO\ldots HumH+Hum(H)_n(SO_4)_m$$

Acidic $SO_2$ coagulates dissolved Humic Acids to solids and forms $Hum(H)_n(SO_4)_m$, which is a complex substance.

$$H_2O+HCl+[H_2O\ldots HumH\ldots(NH_2)_2CO\ldots HumH\ldots H_2O]\text{ --- }HumH++[HumH\ldots(NH_2)_2CO\ldots HumH]+Hum(H)_nCl_m$$

Acidic HCl coagulates dissolved Humic Acids to solids and forms $Hum(H)_nCl_m$ which is a complex substance. After water evaporates from the resulting slurry, the final material is a powder that is collected together with fly ash in the bag house. The Urea Humate based final material is acidic compared with Ammonium Humate based material that is neutral.

There are two extra mechanisms of the reduction of nitrogen oxides to nitrogen which act in the case of the application of either an Ammomia Humate or Ammonium Humate slurry or Urea Humate slurry. The first is based upon aluminum silicates, iron, manganese and other metals present in coal particles which work as a catalyst that increases the rate of $NO_x$ conversion to $N_2$. The second is based upon bitumen present in coal particles. Under high temperature, bitumen decomposes to simple gaseous hydrocarbons which interact with $NO_x$ and reduce it to $N_2$.

HumH, HumNH4, Hum(H)n(SO4)m, Hum(H)nClm, [HumH . . . (NH2)CO . . . HumH] are biologically, geologically and chemically active products which are very beneficial for many types of soil as an ameliorant and conditioner as well as for degraded soil, including desert land and the restoration of disturbed and contaminated soil. However, in this situation, they, as well as (NH4)2SO4 and NH4Cl, are mixed together with the fly ash that contains some toxic heavy metals and some dioxins and furans. Fly ash toxic heavy metals are converted to a bound state due to the following schematic chemical interactions:

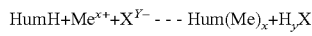

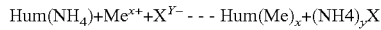

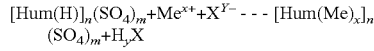

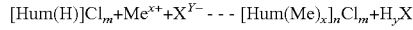

The equations presented above illustrate the cation exchange, chelate and complexes forming mechanism of heavy metals neutralization in form of their cations. Once bound (immobile), the heavy metals have no toxic effects.

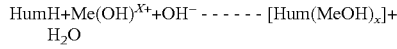

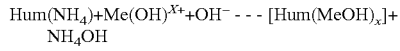

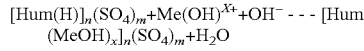

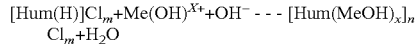

The equations presented above illustrate the cation exchange, chelate and complexes forming mechanism of heavy metals neutralization in form of their hydroxides. Once bound (immobile), the heavy metals have no toxic effects.

These equations present the mechanism of metals hydroxide fixing into Humics based molecules, which also eliminates heavy metals toxicity. These equations work for any heavy metals, including mercury, in their cation form.

Coal burning in power stations also results in elemental mercury emission due to the conversion of metallic and mercury chemical forms into elemental mercury vapor under a temperature around 375 C. Elemental mercury vapor is highly toxic and slightly available for the removing from the flue gases stream. Activated carbon is primarily used for mercury vapor adsorption, but with moderate to low efficacy.

HumH, HumNH4, Hum(H)n(SO4)m, Hum(H)nClm, HumH . . . (NH2)CO . . . HumH] are the form of an organic carbon which is highly absorptive to mercury vapor. Mineral carbon that is a portion of coal's mineral part is highly absorptive to mercury also. Another portion of coal's mineral part, iron oxides and hydroxide, are highly absorptive to elemental mercury as well. The combined action of above mentioned compounds results in a higher rate of mercury removal from the flue gases than just activated carbon. These compounds have as much mercury absorbing capacity as 300 mg per one gram.

Fly ash contains some toxic dioxins and furans, and these are also converted to a bound state due to hydrophobic type of interaction and formation of covalent bonds, resulting in less toxicity. Finally, everything described above converts originally toxic fly ash into useable material, for example, artificial (man-made) ground or technical soil acceptable for many technical applications.

It will be obvious to those skilled in the art that modifications may be made to the embodiments described above without departing from the scope of the present invention.

What is claimed is:

1. A method of preparing a Humic Acid extraction, comprising the steps of:
   (a) introducing material containing Humic Acid into liquid anhydrous ammonia under a pressure greater than atmospheric pressure; and then
   (b) mixing to form a homogeneous slurry.

2. A method of preparing a Humic Acid extraction as recited in claim 1, wherein the material containing Humic Acid is at least one of the group consisting of brown coal, peat, compost, and bottom sediment, and further including the step of grinding the material to a particle size of about 0.1 millimeters in diameter or less.

3. A method of preparing a Humic Acid extraction, comprising the steps of:
   (a) introducing a particulate material containing Humic Acids into a liquid solution consisting of urea and water and then
   (b) mixing the particulate material with the liquid solution consisting of urea and water to form a homogenous slurry.

4. A method of preparing a Humic Acid extraction as recited in claim 3, wherein the material containing Humic Acid is at least one of the group consisting of brown coal, peat, compost, and bottom sediment, and further including the step of grinding the material to a particle size of about 0.1 millimeters in diameter or less.

* * * * *